United States Patent [19]

Clasen

[11] 4,066,698
[45] Jan. 3, 1978

[54] PROCESS FOR THE MANUFACTURE OF ORGANIC HYDRAZINES

[75] Inventor: Hermann Clasen, Falkenstein, Taunus, Germany

[73] Assignee: Hoechst Aktiengesellschaft, Frankfurt am Main, Germany

[21] Appl. No.: 606,108

[22] Filed: Aug. 20, 1975

[30] Foreign Application Priority Data

Aug. 22, 1974 Germany .............................. 2440238

[51] Int. Cl.$^2$ .................. C07C 109/02; C07C 109/04
[52] U.S. Cl. ................................ 260/569; 260/260 N; 260/ 260/293.87; 260/563 R; 260/583 B; 548/361
[58] Field of Search ............................ 260/583 B, 569
[56] References Cited

U.S. PATENT DOCUMENTS 2,806,851  9/1975  Sisler et al. ...................... 260/583 X
2,901,511  8/1959  Hurley ................................. 260/583

OTHER PUBLICATIONS

Stroh, "Methoden der Organischen Chemie", vol. 10, part 2, pp. 30–34, (1967).

Primary Examiner—Robert V. Hines
Attorney, Agent, or Firm—Curtis, Morris & Safford

[57] ABSTRACT

Organic substituted hydrazines are prepared by introducing chloramine optionally carrying one or two alkyl groups into an intensely agitated or finely divided liquid, substantially anhydrous phase of a liquid primary or secondary amine or a solution of a primary or secondary amine in an inert solvent. Especially phenylhydrazine can be obtained in a very good yield from chloramine and aniline. The organic substituted hydrazines are important intermediates for syntheses, especially of pharmaceutical products.

13 Claims, 1 Drawing Figure

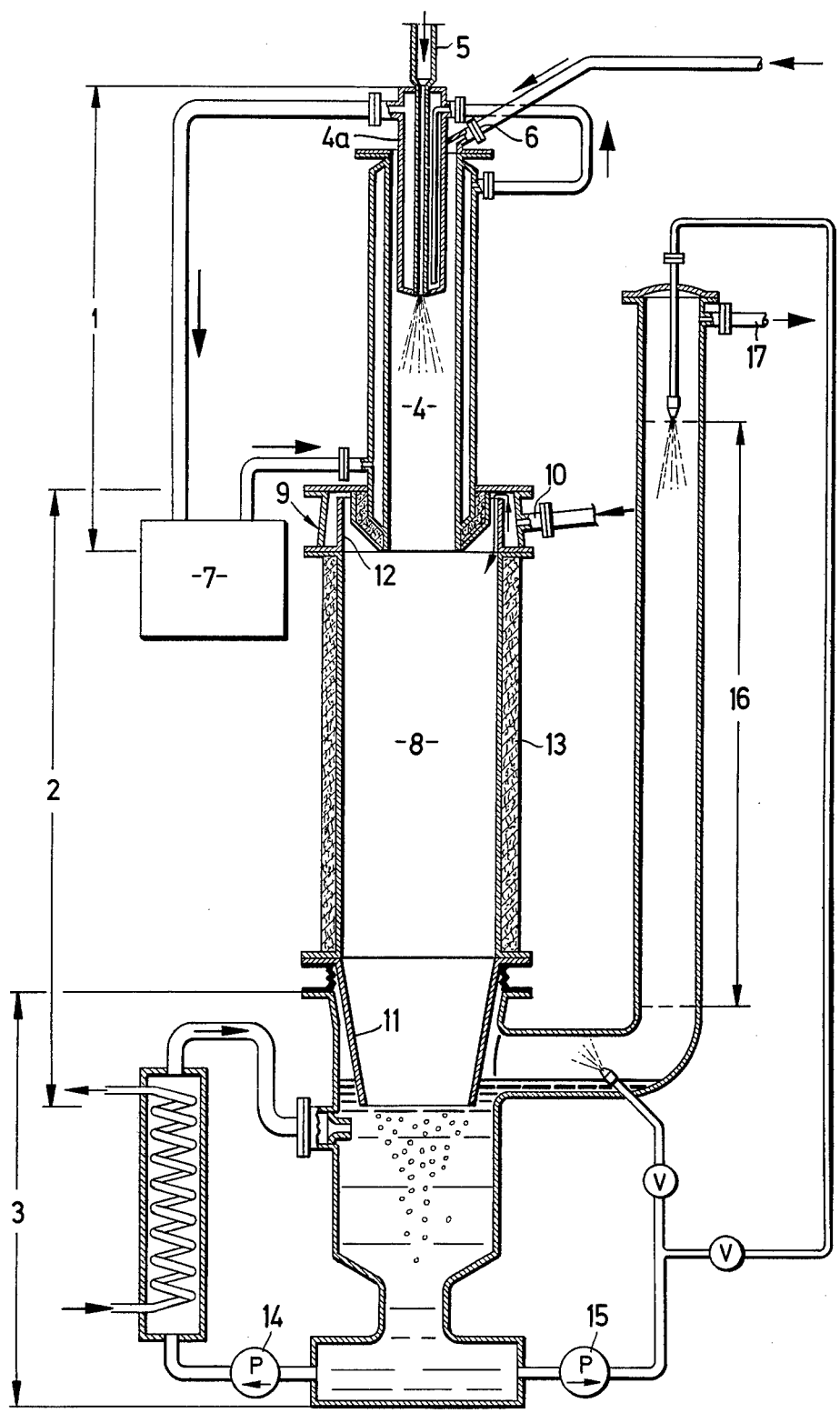

PROCESS FOR THE MANUFACTURE OF ORGANIC HYDRAZINES

This invention relates to an improved process for the manufacture of organic hydrazines.

It is known to prepare organic hydrazines, for example methylhydrazine, phenylhydrazine and the like, by reacting chloramines with primary and secondary aliphatic and cycloaliphatic amines or aniline in the liquid phase under practically anhydrous conditions (cf. Angewandte Chemie 72, (1960), pages 129-130, German Pat. No. 964,865). The aliphatic hydrazines are obtained in a good yield, but in can be gathered from the original literature cited in the above references that the concentrations of organic hydrazine are very low (0.2% by weight only). Due to the low concentration this mode of preparation is very uneconomical. When the reaction is carried out with aniline at low concentrations insufficient yields of phenylhydrazine are likewise obtained. In the example of the aforesaid German patent describing the reaction of chloramine with aniline no yield of phenylhydrazine is indicated. It can be assumed that considerable amounts of secondary products are formed, for example phenylene diamines and chloranilines.

In J. Org. Chem. 26 (1961), page 281 a yield of phenylhydrazine of 46% is reported for the reaction of chloramine with aniline under anhydrous conditions, calculated on the reacted aniline. But this statement is not consistent with the given amounts, i.e. 1.1 g of crude phenylhydrazine from 3.1 g of consumed aniline. The calculated yield amounts to 31% of the theory only, referred to the consumed aniline and referred to the chloramine (50 mmoles) used the calculated yield is only 20%. The phenylhydrazine concentration in the aniline is 2.6% by weight.

In view of the considerable industrial importance of organic hydrazines, especially of phenylhydrazines, as starting compounds for further syntheses, above all in the field of pharmaceuticals, it has been desirable to render more economic the known reaction of chloramines with primary and secondary amines in the liquid phase under practically anhydrous conditions, i.e. considerably to improve the yield of organic hydrazines without any greater additional technological effort.

According to the present invention the problem is solved by intensely agitating or finely dividing the liquid phase containing the primary or secondary amine during the introduction of the chloramine.

The present invention therefore provides a process for the manufacture of organic substituted hydrazines by introducing unsubstituted chloramine or a chloramine substituted by one or two alkyl groups into a liquid substantially anhydrous phase consisting of a liquid primary or secondary amine or a primary or secondary amine dissolved in an inert solvent, which comprises intensely agitating or finely dividing the liquid phase during the introduction of the chloramine.

Suitable chloramines in the process of the invention are, besides the unsubstituted chloramine $ClNH_2$ itself, chloramines carrying one or two alkyl groups as substituents, for example methyl chloramine, n-propyl chloramine, i-butyl chloramine, diethyl chloramine, which can be prepared in known manner, for example as described in "Allgemeine und Praktische Chemie" 21 (1970), pages 123-124; "Chemikerzeitung/Chemische Apparatur" 92 (1968), pages 383 et seq. or U.S. Pat. No. 2,808,439.

In their preparation the chloramines are all obtained in admixture with ammonia or the primary or secondary starting amines used and an inert gas such as nitrogen, optionally also in admixture with finely divided ammonium chloride or the hydrochloride of the starting amine. The chloramine containing gas mixture is introduced into the intensely agitated or finely divided liquid and substantially anhydrous phase consisting of the liquid primary or secondary amine used or of a solution of the said amine in an inert solvent, or it is passed over the liquid phase.

Suitable primary and secondary amines are aliphatic, cycloaliphatic, aromatic and araliphatic amines such as, for example, n-butyl amine, n-hexyl amine, cyclohexyl amine, piperidine, piperazine, aniline, diphenyl amine, o-toluidine, o-anisidine, benzidine, and preferably aniline. The amines can be used as such in liquid form or in the form of a solution in an inert solvent such as aliphatic or aromatic hydrocarbons and halohydrocarbons, for example n-hexane, petroleum ether, benzene, toluene, chlorobenzene; ethers such as diethyl ether, dioxane, or tetrahydrofurane. The use of a solvent is preferred with amines having a high melting point.

The water content of the liquid phase should not exceed noticeably about 0.5% by weight since higher water contents diminish the yield of the desired organic hydrazines. If the amines or solvents used are difficult to prepare in anhydrous form known substances, such as glue or gelatin, are added as heavy metal acceptors to counteract the unfavorable influence of water.

Due to the intense agitation of the liquid phase the chloramine containing gas current may surprisingly have a temperature up to about 300° C, while the temperature of the liquid phase should not exceed substantially 150° C. The temperature to be chosen depends, in the first place, on the boiling points of the amine and of the solvent, if any. The lower temperature limit of the gas current and of the liquid phase is essentially determined by the fact that at too low a temperature the reaction speed is too slow. Hence, an acceptable lower limit is approximately room temperature.

The essential characteristic of the present invention is the intense agitation or the fine division of the liquid phase during the introduction of the chloramine or the chloramine containing gas current. The intense agitation is preferably brought about by stirring and/or circulation by pumping and/or vaporization and/or intense shaking of the liquid in a vibration mixer.

To finely divide the liquid phase it is preferably introduced through a nozzle into the constricted section of a preferably vertical Venturi tube through which the chloramine-(containing)-gas current streams in downward direction. According to relevant manuals a Venturi tube is a tube that has flaring ends connected by a constricted middle section forming a throat. As a result of the constriction, the speed of a gaseous or liquid medium flowing through the tube is increased with decreasing pressure and in the enlarged end the original conditions are approximately adjusted again. When, in the present case, the chloramine-(containing)-gas current comes into contact with the liquid phase introduced through a nozzle in the constriction of the Venturi tube the liquid phase is especially intensely agitated in this section and finely divided owing to the increased gas speed. As a result of the strong molecule movement in the individual droplets of the liquid the organic hydrazine formed at the surface is rapidly transported into the interior of the droplets.

When, according to a preferred embodiment of the process of the invention, unsubstituted chloramine is introduced into anhydrous aniline to prepare phenylhydrazine, care should be taken that the phenylhydrazine content of the liquid phase does not exceed essentially about 6% by weight, as otherwise the chloramine would react further with the phenylhydrazine to hydrazobenzene and with the latter to further secondary products (up to benzene). In analogous manner definite concentrations should not be exceeded with the use of other primary and secondary amines. These concentrations are slightly different from case to case but could be readily determined by an expert by a few routine experiments.

If hydrazobenzene (N,N'-diphenylhydrazine) is the desired product in the reaction of the unsubstituted chloramine with aniline, the concentration has to be varied accordingly. The same applies to the reaction with other amines.

The reaction mixture is worked up in usual manner as in the case of the known processes without intense agitation or fine division of the liquid phase. When the unsubstituted chloramine is reacted with aniline to yield phenylhydrazine the ammonium chloride formed is mechanically separated by filtration, sedimentation or centrifugation and prior to rectification the filtrate is treated with alkali metal or alkali earth metal compounds. The phenyl-hydrazine is separated from the aniline and small amounts of by-products by rectification. The distillation residue always contains small amount of hydrazobenzene which crystallizes on cooling. The yields of phenylhydrazine amounts to more than 70% of the theory, calculated on the reacted aniline. Similarly high and still higher yields can be obtained by using anilines carrying one substituent in the nucleus and having a dipole moment of about 1.4 to 1.9 Debye. Of course, there are starting materials with which the yields are lower, as is the case with all types of reactions, but in any case the yields obtained are considerably above those obtained when the same starting compounds are reacted with chloramine in known manner, i.e. without intense agitation or fine division of the liquid phase. The reaction according to the invention is preferably carried out discontinuously; however, it can also be performed with a good result in continuous manner, for example with counter-current flow of the gaseous and liquid phases.

The reason for the increase in the yield achieved by intense agitation or fine division of the liquid phase during the introduction of chloramine was examined with the reaction of unsubstituted chloramine and aniline to yield phenylhydrazine. It has been found that the chloramine reacts more quickly with the formed phenylhydrazine than with aniline and, therefore, if the phenylhydrazine remains for a prolonged period of time at its site of formation, i.e. where it comes into contact with the chloramine, it is preferably reacted further to hydrazobenzene and other products reducing the yield. In the process of the invention these undesired reactions are avoided by removing the formed phenylhydrazine as quickly as possible from the place where the chloramine comes into contact with the liquid phase. By the contact of the chloramine with the finely divided liquid phase secondary reactions of the phenylhydrazine with chloramine are reduced not only by the strong movement of the molecules in the liquid droplets but also by the enlargement of the liquid surface, since the enlargement of the surface results in a diminished surface distribution of the hydrazine whereby the probability is increased that the following chloramine molecule comes into contact with an amine molecule and not with a hydrazine molecule so that further hydrazine is formed and not reacted.

Owing to the rapid removal of the phenylhydrazine and the enlargement of the surface of the liquid phase by the fine division the phenylhydrazine can accumulate in the liquid phase to a much higher degree as hitherto usual without any decrease in yield but even with higher yields. Due to the better economy resulting therefrom the process according to the invention is even superior to the conventional process for the manufacture of phenylhydrazine according to E. Fischer (reduction of diazotized aniline with sulfite, or it can at least compete therewith.

The organic hydrazines prepared by the process of the invention are important intermediates for a number of syntheses, above all of pharmaceutical products. In the first place, phenylhydrazine is an important starting material, for example for the known reaction with acetoacetic acid esters to produce pyrazolones. For this reaction the phenylhydrazine need not be separated from the aniline solution.

A device suitable to carry out the process of the invention is diagrammatically illustrated by way of example in the accompanying drawing. The device is composed of three essential elements: the chloramine generator 1, the cooling zone 2 and the amine reactor 3. The chloramine generator 1 comprises as essential parts a reaction cell 4 made of nickel and a nozzle 4a also made of nickel through the axial tube 5 of which chlorine is introduced into the reaction cell. Inlet 6 serves to introduce ammonia or the respective amine. Together with chlorine, ammonia and/or the amine an inert diluting gas may be introduced, for example nitrogen. The reaction cell 4 and the chlorine nozzle 4a are heated by oil-fed circulation heating 7 passing hot oil through the jacket of the reaction cell and of the chlorine nozzle. When chlorine is reacted with ammonia, the heating temperature is about 320° C. The chloramine generator 1 is directly followed by cooling part 2 which comprises a cylindrical vessel 8 with means 9 for the introduction of a cooling medium through inlet 10 and a funnel-shaped bottom part 11. The cooling medium supplied through inlet 10 is deflected on guide ring 12 and flows in the direction of the gas stream leaving the chloramine generator. Cylindrical vessel 8 is preferably surrounded by an insulating jacket 13 made of any known insulating material. The funnel-shaped outlet 11 of cooling section 2 extends below the surface of the liquid phase in amine vessel 3. Pump 14 produces a liquid jet in transverse direction to the point of introduction and pump 15 produces a liquid counter-current to the issuing gas stream. The issuing gas current is further treated in countercurrent flow over a trickling column 16 by a liquid downdraft of pump 15. The off-gas is discharged from trickling column 16 through outlet 17.

The following examples illustrate the invention.

EXAMPLE 1

To carry out the process of the invention a device as described above was used.

The chloramine generator heated by circulating oil heating 7 to 320° C was charged, through inlet 5 of chlorine nozzle 4a with 220 N liters Cl$_2$ per hour (N meaning measured under normal conditions of pressure and temperature) and through inlet 6 with 1.5Nm³ NH₃ per hour. Nitrogen was used as cooling medium and introduced into cooling section 2 through inlet 10 in an amount of 12 Nm³ per hour. At baffle ring 12, a coaxial nozzle insert, the nitrogen current was deflected, first in upward direction and then downward so that it streamed uniformly and coaxially through the narrow annular slit between baffle ring 12 and the heat-insulated end section of reaction cell 3 into cylindrical vessel 8 of cooling section 2. The nitrogen current surrounded the hot chloramine containing gas current issuing from reaction cell 3. The two parallel gas currents mixed with each other, the temperature of the chloramine containing current dropped and the ammonium chloride separated in a very finely divided form. The nitrogen current near the wall was so vigorous and the diameter of cylindrical vessel 8 (150 mm) so large that no hot portions came into contact with the inner wall of vessel 8. In this manner a deposit of ammonium chloride was avoided on the inner wall of vessel 8 and in the funnel-shaped bottom part 11. The chloramine and ammonium chloride containing gas current mixed with the cooling gas was passed through outlet 11 of the cooling section directly into liquid aniline. Two rotary pumps 14 and 15 each having a capacity of about 6m³ per hour and a gas entraining effect ensured a very vigorous agitation of the aniline which was used in total amount of 17.14 kg and contained 0.095% by weight of water. The off-gas leaving outlet 17 of trickling column 16 was substantially free of ammonium chloride and chloramine.

The reaction conditions are indicated in the following table.

$NH_3$ was driven out by blowing in $N_2$ under a pressure of 100 mm Hg, benzene, the water-aniline azeotrope and the aniline and then, at a sump temperature of up to 160° C and while further reducing the pressure, the phenylhydrazine were distilled off.

The amount of pure phenylhydrazine obtained corresponded to 95% of the iodometrically determined content. Pure hydrazobenzene could be obtained by crystallization from the distillation residue.

After partial condensation the off-gas was recycled, nitrogen and benzene were discharged.

In the following table some of the important data of the process of the present invention according to Example 1 are compared with corresponding data of the state of the art.

| | Comparison | |
|---|---|---|
| | according to invention | according to J.Org.Chemie 26 (1961) page 821 |
| concentration % by weight phenylhydrazine | 4.2 | 2.6 |
| Yield β (mole %) | 42 | 20 |
| Yield γ (mole %) | 80 | 31 |

EXAMPLE 2

The reaction was carried out in the device described above. Instead of aniline, 17.21 kg o-toluidine were used and the further experimental conditions were as follows:

375 Nl Cl₂ per hour
2.6 Nm³ per hour

TABLE

| reaction time (minutes) | gas temperature prior to coming into contact with aniline ° C | temperature of agitated aniline ° C | temperature of circulating heating oil ° C in | temperature of circulating heating oil ° C out | N₂ pressure before nozzle 10 atm. gauge | content of phenylhydrazine in aniline (% by weight) | yields α | yields β | yields γ |
|---|---|---|---|---|---|---|---|---|---|
| 0 | 94 | 19 | 310 | 285 | 0.02 | | | | |
| 15 | 108 | 19 | 316 | 292 | 0.02 | | 0.71 | | |
| 30 | 120 | 20 | 320 | 295 | 0.02 | 1.4 | | 0.58 | |
| 42 | 122 | 20 | 322 | 296 | 0.03 | | 0.72 | | |
| 60 | 125 | 20 | 323 | 297 | 0.03 | 2.5 | | 0.51 | |
| 73 | | | | | | | 0.73 | | |
| 90 | 134 | 20 | 324 | 298 | 0.03 | 3.0 | | 0.41 | |
| 120 | 136 | 20 | 325 | 299 | 0.03 | 4.2 | | 0.42 | 0.80 |

Referring to the table:
α designates the molar ratio of chloramine (the chloramine content is determined iodometrically in a gas sample taken at the end of cooling vessel 8) to the chlorine consumed.
β designates the molar ratio of the phenylhydrazine (determined iodometrically in the aniline) to the chloramine (determined as described for α).
γ is the molar ratio of the phenylhydrazine to the consumed aniline.

Besides phenylhydrazine small amounts of benzene, nitrogen and hydrazobenzene were formed from the aniline but no chlorinated organic compounds.

In the preparation of the chloramine ammonium chloride and nitrogen were formed. The fact that β is smaller than γ indicates that in the liquid aniline the chloramine partially decomposes into ammonium chloride and nitrogen.

To work up the reaction mixture the dispersed ammonium chloride was separated by filtration and the filtrate mixed with 100 g of 30% NaOH. The dissolved 10 Nm³ cooling N₂ per hour
temperature of the oil flowing into the heating jacket of the reaction cell: 327° C
temperature of the oil leaving the heating jacket of the chlorine nozzle 4: 307° C
temperature of o-toluidine 40° C
reaction time about 70 minutes The o-tolylhydrazine was obtained in the form of a 5.0% solution. The molar ratio of the iodometrically titrated o-tolylhydrazine to the chloramine used (β) was 0.75 and the molar ratio of o-tolylhydrazine to the consumed toluidine (γ) was about 0.85%. Both results were better than in the phenylhydrazine preparation according to Example 1 and o-tolylhydrazine content in the reaction solution increased more rapidly.

If o-tolylhydrazine is separated by rectification in the same manner as the phenylhydrazine of Example 1 considerable losses occur by decomposition and, therefore, the o-tolylhydrazine solution in o-toluidine was filtered to separate the ammonium chloride, methanol and water were added and the solution was directly reacted at 85° C over a period of 2 hours with the stoichiometric amount of acetoacetic acid methyl ester whereby 1-o-tolyl-3-methyl-pyrazol-5-one was obtained in a yield of 88% of the theory. It is very surprising that this reaction could be carried out with such a high yield of the pyrazolone derivative as one could expect that the excess o-toluidine would simultaneously react with the acetoacetic acid ester.

EXAMPLE 3

The device as used in Example 1 was charged with 21.8 kg of freshly distilled o-anisidine having a water content of 0.12% by weight. The other reaction conditions were as follows:

375 Nl $Cl_2$ per hour
2.63 $Nm^3$ $NH_3$ per hour
10 $Nm^3$ $N_2$ per hour as cooling medium
temperature of the circulated heating oil: about 325° C
reaction time: about 70 minutes After an introduction time of 70 minutes of the chloramine into the o-anisidine the latter contained 4.3% by weight o-methoxyphenylhydrazine.

The average values were as follows:

$\alpha$ 0.86
$\beta$ 0.49 and
$\gamma$ 0.80 to 0.85

Owing to the fact that the o-methoxyphenylhydrazine is not stable at elevated temperature and difficult to distil without decomposition it is recommended in this case, too, to prepare the corresponding pyrazolone by direct reaction with acetoacetic acid ester of the solution in o-anisidine.

What is claimed is:

1. A process for the preparation of organic hydrazines which comprises introducing a gaseous chloramine selected from the group consisting of chloramine, monoalkyl chloramine and dialkyl chloramine into a substantially anhydrous liquid phase organic amine selected from the group consisting of primary amine and secondary amine while intensely agitating the liquid phase during the addition of the chloramine and selectively reacting the chloramine with the organic amine to form the corresponding organic hydrazine.

2. The process of claim 1 wherein the liquid phase temperature is between about room temperature to about 150° C.

3. The process of claim 1 wherein the gas phase temperature is between about room temperature to about 300° C.

4. The process of claim 1 wherein the chloramine is a member selected from the group consisting of methyl chloramine, n-propyl chloramine, i-butyl chloramine and diethyl chloramine.

5. The process of claim 1 wherein the organic amine is a member selected from the group consisting of n-butyl amine, n-hexyl amine, cyclohexyl amine, piperidiene, piperazine, aniline, diphenyl amine, o-toluidine, o-anisidine and benzidine.

6. The process of claim 1 wherein chloramine is used and the organic amine is a member selected from the group consisting of aniline, o-toluidine and o-anisidine.

7. A process for the preparation of organic hydrazines which comprises contacting, under conditions of intense liquid agitation, a gaseous chloramine selected from the group consisting of chloramine, monoalkyl chloramine and dialkyl chloramine with a substantially anhydrous organic amine selected from the group consisting of primary amine and secondary amine in finely divided liquid phase and selectively reacting the chloramine with the organic amine to form the corresponding organic hydrazine.

8. The process of claim 7 wherein the gaseous chloramine is contacted co-currently with the liquid phase organic amine by introducing the organic amine through a nozzle into a constricted section of a venturi tube through which the chloramine gas is passing.

9. The process of claim 7 wherein the liquid phase temperature is between room temperature to about 150° C.

10. The process of claim 7 wherein the gas phase temperature is between about room temperature to about 300° C.

11. A process of the preparation of organic hydrazines which comprises introducing a gaseous chloramine selected from the group consisting of chloramine, monoalkyl chloramine and dialkyl chloramine into a substantially anhydrous liquid phase organic amine selected from the group consisting of primary and secondary amine and selectively reacting the chloramine with the organic amine at a liquid phase temperature between about room temperature and 150° C and a gas phase temperature between about room temperature and about 300° C to form the corresponding organic hydrazine while intensely agitating the liquid phase during the addition of the chloramine to reduce contact of organic hydrazine product with chloramine reactant and maintaining the content of the organic hydrazine in the reaction mixture below about 6% by weight of the reaction mixture.

12. A process for the preparation of organic hydrazines which comprises contacting a gaseous chloramine selected from the group consisting of chloramine, monoalkyl chloramine and dialkyl chloramine with a substantially anhydrous organic amine selected from the group consisting of primary amine and secondary amine in finely divided liquid phase and selectively reacting the chloramine with the organic amine at a liquid phase temperature between about room temperature to about 150° C and a gas phase temperature between about room temperature and about 300° C to form the corresponding organic hydrazine while intensely agitating the liquid phase during the addition of the chloramine to reduce contact of organic hydrazine product with the chloramine reactant and maintaining the content of the organic hydrazine in the reaction mixture below about 6% by weight of the reaction mixture.

13. The process as claimed in claim 1, wherein unsubstituted chloramine is introduced into substantially anhydrous aniline.

* * * * *